(12) United States Patent
Koshijima (10) Patent No.: US 10,617,573 B2
(45) Date of Patent: Apr. 14, 2020

(54) STRETCHABLE LAMINATE SHEET AND DISPOSABLE WORN ARTICLE

(71) Applicant: ZUIKO CORPORATION, Osaka (JP)

(72) Inventor: Miwa Koshijima, Osaka (JP)

(73) Assignee: ZUIKO CORPORATION, Osaka (JP)

( * ) Notice: Subject to any disclaimer, the term of this patent is extended or adjusted under 35 U.S.C. 154(b) by 387 days.

(21) Appl. No.: 15/557,121

(22) PCT Filed: May 12, 2016

(86) PCT No.: PCT/JP2016/064154
§ 371 (c)(1),
(2) Date: Sep. 10, 2017

(87) PCT Pub. No.: WO2016/185999
PCT Pub. Date: Nov. 24, 2016

(65) Prior Publication Data
US 2018/0042784 A1  Feb. 15, 2018

(30) Foreign Application Priority Data

May 19, 2015 (JP) .................................. 2015-101640

(51) Int. Cl.
*A61F 13/49* (2006.01)
*B32B 7/05* (2019.01)
(Continued)

(52) U.S. Cl.
CPC ........ *A61F 13/49007* (2013.01); *A61L 15/22* (2013.01); *A61L 15/42* (2013.01);
(Continued)

(58) Field of Classification Search
CPC .......... A61F 13/49007; A61F 13/49011; A61F 13/49012; A61F 13/4902; A61F 13/49061;
(Continued)

(56) References Cited

U.S. PATENT DOCUMENTS 4,859,519 A * 8/1989 Cabe, Jr. ................ A61F 13/512
428/131
5,964,742 A * 10/1999 McCormack ............ D04H 1/54
604/380

(Continued)

FOREIGN PATENT DOCUMENTS

CN  1779300 A  4/1998
JP  H10-029259 A  2/1998
(Continued)

OTHER PUBLICATIONS

International Search Report Issued in PCT/JP2016/064154 dated Aug. 16, 2016.
(Continued)

*Primary Examiner* — Catharine L Anderson
(74) *Attorney, Agent, or Firm* — Renner, Otto, Boisselle & Sklar, LLP (57) ABSTRACT

A stretchable laminate sheet including a thermoplastic stretchable film laminated on a non-woven fabric containing thermoplastic fiber therein, wherein: the non-woven fabric and the stretchable film are welded together at a plurality of first and second welding portions; the first welding portions are longer in a first direction and are shorter in a second direction perpendicular to the first direction; and the second welding portions are longer in a third direction crossing the first direction and are shorter in a fourth direction perpendicular to the third direction.

5 Claims, 10 Drawing Sheets (51) Int. Cl.
  *B32B 7/04* (2019.01)
  *B32B 7/14* (2006.01)
  *B32B 3/30* (2006.01)
  *B32B 5/24* (2006.01)
  *A61L 15/22* (2006.01)
  *A61L 15/42* (2006.01)
  *B32B 5/02* (2006.01)
  *B32B 27/08* (2006.01)
  *B32B 27/12* (2006.01)
  *B32B 5/22* (2006.01)
  *B32B 7/08* (2019.01)
  *B32B 27/06* (2006.01)
  *B32B 5/26* (2006.01)
  *A61F 13/15* (2006.01)

(52) U.S. Cl.
  CPC ............... *B32B 3/30* (2013.01); *B32B 5/022* (2013.01); *B32B 5/24* (2013.01); *B32B 7/04* (2013.01); *B32B 7/05* (2019.01); *B32B 7/14* (2013.01); *B32B 27/08* (2013.01); *B32B 27/12* (2013.01); *A41B 2400/52* (2013.01); *A41D 2400/52* (2013.01); *A61F 13/15739* (2013.01); *A61F 2013/49046* (2013.01); *B32B 5/22* (2013.01); *B32B 5/26* (2013.01); *B32B 7/08* (2013.01); *B32B 27/06* (2013.01); *B32B 2262/02* (2013.01); *B32B 2307/51* (2013.01); *B32B 2307/724* (2013.01); *B32B 2307/726* (2013.01); *B32B 2307/7265* (2013.01); *B32B 2555/02* (2013.01)

(58) Field of Classification Search
  CPC .. A61F 2013/49022; A61F 2013/49023; A61F 2013/51078; A61F 2013/5108; A61F 2013/51083; A61F 2013/51085
  See application file for complete search history.

(56) References Cited

U.S. PATENT DOCUMENTS

| | | | |
|---|---|---|---|
| 6,537,930 | B1 | 3/2003 | Middlesworth et al. |
| 8,188,333 | B2 * | 5/2012 | Matsuoka .......... A61F 13/15731 |
| | | | 156/229 |
| D696,869 | S * | 1/2014 | Rhodes, III ...................... D5/58 |
| 9,283,125 | B2 * | 3/2016 | Otsubo ............. A61F 13/51401 |
| 2002/0156444 | A1 | 10/2002 | Otsubo |
| 2005/0148990 | A1 * | 7/2005 | Shimoe ............. A61F 13/15203 |
| | | | 604/396 |
| 2008/0095978 | A1 | 8/2008 | Siqueira et al. |
| 2010/0262105 | A1 | 10/2010 | Turner |
| 2013/0226120 | A1 | 8/2013 | Van De Maele |
| 2014/0130956 | A1 | 5/2014 | Floberg et al. |
| 2017/0231839 | A1 * | 8/2017 | Tashiro ................ A61F 13/515 |
| | | | 604/385.3 |

FOREIGN PATENT DOCUMENTS

| | | |
|---|---|---|
| JP | 2005-245483 A | 9/2005 |
| JP | 2009-153913 A | 7/2009 |
| JP | 2009-207698 A | 9/2009 |
| JP | 2013-233383 A | 11/2013 |
| JP | 2014-124477 A | 7/2014 |
| JP | 2014-129613 A | 7/2014 |
| JP | 2014-520589 A | 8/2014 |
| JP | 2014-188129 A | 10/2014 |
| JP | 2015-043895 A | 3/2015 |
| JP | 2015-136820 A | 7/2015 |

OTHER PUBLICATIONS

Extended European Search Report for corresponding App. No. 16796392.5, dated Dec. 14, 2018.
Second Chinese Office Action dated Jul. 31, 2019 for corresponding Chinese Application No. 201680016098.7.

* cited by examiner

STRETCHABLE LAMINATE SHEET AND DISPOSABLE WORN ARTICLE

TECHNICAL FIELD

The present invention relates to a stretchable laminate sheet for use in a disposable worn article or a part thereof.

BACKGROUND ART

Stretchable laminate sheets including a non-woven fabric laminated with a stretchable film are well known in the art.

As a structure for laminating together a non-woven fabric and a stretchable film, a large number of circular welding portions or oblong welding portions, for example, are arranged in a predetermined pattern (the first patent document).

CITATION LIST

Patent Literature

[First Patent Document] U.S. Pat. No. 6,537,930B1 (WO2001/087592A)

SUMMARY OF INVENTION

A stretchable film itself is not air-permeable by nature. Therefore, when a tension is applied on a stretchable laminate sheet, holes will not be formed in the film around welding portions, if the strength of the film is high, thereby deteriorating the air-permeability. On the other hand, if the film strength is low, holes will be formed in the film around edges of many welding portions. Then, the air-permeability will be good but the stretchability is likely to lower.

It is therefore an object of the present invention to provide a stretchable laminate sheet having a good air-permeability and a good stretchability.

A stretchable laminate sheet of the present invention is a stretchable laminate sheet including a thermoplastic stretchable film laminated on a non-woven fabric containing thermoplastic fiber therein, wherein:

the non-woven fabric and the stretchable film are welded together at a plurality of first welding portions and a plurality of second welding portions;

the first welding portions each have a longer first length in a first direction, and each have a first width, shorter than the first length, in a second direction perpendicular to the first direction; and the second welding portions each have a longer second length in a third direction crossing the first direction, and each have a second width, shorter than the second length, in a fourth direction perpendicular to the third direction.

The first welding portions have an elongate shape.

When a tension is applied in the second direction perpendicular to the first direction, which is the longitudinal direction of the first welding portions, the film is pulled around edges of the first welding portions, and holes are likely to be formed in the film. When a tension is applied in the first direction on the first welding portions, holes are unlikely to be formed in the film around edges of the first welding portions. That is, as the direction of the tension acting on the first welding portions is closer to the second direction perpendicular to the longitudinal direction, a greater force acts over a wide area of the edges of the first welding portions along the first direction.

For example, when a tension is applied in the second direction, holes are likely to be formed in the film in areas along edges along the longitudinal direction of the first welding portions, and large holes are likely to be formed.

The second welding portions have an elongate shape.

When a tension is applied in the fourth direction perpendicular to the third direction, which is the longitudinal direction of the second welding portions, the film is pulled around edges of the second welding portions, and holes are likely to be formed in the film. When a tension is applied in the third direction on the second welding portions, holes are unlikely to be formed in the film around edges of the second welding portions.

With the second welding portions whose longitudinal direction extends in the third direction crossing the first direction, as the longitudinal direction is closer to the direction (the second direction) perpendicular to the first direction, the range along the first direction of the tension acting on the second welding portions when a tension is applied in the second direction becomes smaller. Therefore, when a tension is applied in the second direction, holes are unlikely to be formed in the film in areas along the longitudinal direction of the second welding portions, and large holes are unlikely to be formed.

Now, when a tension including a component in the second direction is applied to the stretchable laminate sheet, the size of a hole to be formed in the film in an area along the edge of a first welding portion is different from the size of a hole to be formed in the film in an area along the edge of a second welding portion. Therefore, by appropriately setting the first and third directions of the first and second welding portions, it is possible to realize a stretchable laminate sheet having an intended air-permeability and an intended stretchability.

In the present invention, the holes in the stretchable laminate sheet may be formed during the manufacturing process, or may be formed during use of the product, e.g., when the worn article is put on.

BRIEF DESCRIPTION OF DRAWINGS

In FIG. 5A to FIG. 10A, welding portions are shown in solid black so that they are easy to see. In FIG. 2A, FIG. 2B, FIG. 3 and FIG. 5B to FIG. 10B, welding portions are depicted in solid line.

DESCRIPTION OF EMBODIMENTS

Preferably, the first welding portions and the second welding portions are arranged along sides, excluding corners, of virtual polygonal shapes each having four or more sides, and each area surrounded by the corners of the polygonal shapes and the first welding portions and the second welding portions is a non-welding portion where the non-woven fabric and the stretchable film are not welded together.

A polygonal shape has a greater SA/L value, which is obtained by dividing the area SA by the length L of each side, than a triangle. Therefore, the area of the non-welding portion within the virtual polygonal shape where there is no hole will be large, resulting in a good stretchability. Therefore, the welding portions will not be arranged closely together but will be arranged sparsely, thereby increasing the welding pressure with ultrasonic energy, or the like, in the welding portions, and increasing the reliability of the welding.

Even more preferably, the virtual polygonal shape is a rectangular shape, a hexagonal shape, an octagonal shape, or a combination of these shapes.

In these cases, the first and second welding portions can easily be arranged.

Preferably, the disposable worn article includes: a girth portion formed from the stretchable laminate sheet, extending in a girth direction of a wearer, and configured to cover a torso of the wearer; and an absorbent body configured to cover a crotch of the wearer;

the girth portion includes a lower edge portion, an upper edge portion, and a middle portion between the lower edge portion and the upper edge portion;

the first welding portions are provided in the lower edge portion and the middle portion;

the second welding portions are provided in the upper edge portion;

the first welding portions are arranged intermittently in the girth direction and arranged intermittently in a vertical direction perpendicular to the girth direction;

the second welding portions are arranged intermittently in the girth direction and arranged intermittently in the vertical direction;

a length of each of the first welding portions in the vertical direction perpendicular to the girth direction is longer than a length of each of the first welding portions in the girth direction; and a length of each of the second welding portions in the girth direction is longer than a length of each of the second welding portions in the vertical direction.

The first welding portions that are longer in the vertical direction are provided in a matrix pattern in the lower edge portion and in the middle portion of the girth portion. Therefore, if a great tension acts in the girth direction when the worn article is put on, holes are likely to be formed in the film in areas along edges in the girth direction of the first welding portions, thereby improving the air-permeability.

On the other hand, the second welding portions that are longer in the girth direction are provided in the upper edge portion of the girth portion. Therefore, when a great tension acts in the girth direction by the act of putting the worn article on, holes are unlikely to be formed in the film in areas along the girth direction of the second welding portions. Therefore, large holes are unlikely to be formed, and it is easy to ensure the stretchability.

More preferably, the girth portion includes an overlap portion where the absorbent body is laid on the girth portion;

the non-woven fabric and the stretchable film are welded together at a plurality of third welding portions in the overlap portion;

the third welding portions each have a longer third length in the vertical direction, which is the first direction, and have a third width, shorter than the third length, in the girth direction, which is the second direction; and the third length of the third welding portions is longer than the first length of the first welding portions.

The overlap portion where the absorbent body is laid on the girth portion has a high rigidity. Therefore, if the overlap portion stretches and shrinks in the girth direction, it may lower the wearability, etc.

In the present example, the third length in the vertical direction of the third welding portions in the overlap portion is longer than the first length in the vertical direction of the first welding portions. Therefore, if a great tension acts in the girth direction when the worn article is put on, holes are likely to be formed in the film in areas along edges in the girth direction of the third welding portion. Therefore, large holes are likely to be formed, and an elasticity is unlikely to be present in the overlap portion.

Even more preferably, the third width of the third welding portions is smaller than the first width of the first welding portions.

In this case, the third width, smaller than the first width, prevents the area of the third welding portions from increasing. Therefore, at the third welding portions in the overlap portion, as compared with the first welding portions adjacent to the overlap portion, a significant change in energy during welding is unlikely to occur, making it easier to perform ultrasonic welding at the third welding portions, for example.

Even more preferably, a ratio of the third length of the third welding portions with respect to the third width of the third welding portions is greater than a ratio of the first length of the first welding portions with respect to the first width of the first welding portions.

In this case, the third length ratio, which is greater than the first length ratio, prevents the area of the third welding portions from increasing. Therefore, again, it is made easier to perform ultrasonic welding at the third welding portions.

Preferably, the girth portion includes an overlap portion where the absorbent body is laid on the girth portion;

the non-woven fabric and the stretchable film are welded together at a plurality of third welding portions in the overlap portion;

a fourth region is arranged between a first region where the first welding portions are provided and a third region where the third welding portions are provided, and the non-woven fabric and the stretchable film are welded together at a plurality of fourth welding portions in the fourth region; and a ratio of a total area of the fourth welding portions with respect to an area of the fourth region is greater than a ratio of a total area of the first welding portions with respect to an area of the first region and is less than a ratio of a total area of the third welding portions with respect to an area of the third region.

In this case, the total area of welding portions with respect to the total area of the region decreases in this order: the third region, the fourth region and the first region. Therefore, the welding area changes gradually in the girth direction. Thus, it is made easier to perform ultrasonic welding at the welding portions.

Any feature illustrated and/or depicted in conjunction with one of the aforementioned aspects or the following embodiments may be used in the same or similar form in one or more of the other aspects or other embodiments, and/or may be used in combination with, or in place of, any feature of the other aspects or embodiments.

Embodiments

The present invention will be understood more clearly from the following description of preferred embodiments taken in conjunction with the accompanying drawings. Note however that the embodiments and the drawings are merely illustrative and should not be taken to define the scope of the present invention. The scope of the present invention shall be defined only by the appended claims. In the accompanying drawings, like reference numerals denote like components throughout the plurality of figures.

An embodiment of the present invention will now be described with reference to the drawings.

The present stretchable laminate sheet can be used for various applications. The present stretchable laminate sheet, applied to a disposable diaper, will now be described by way of example. The diaper includes a girth portion covering the torso of the wearer, and a crotch portion covering the crotch of the wearer. The stretchable laminate sheet is used in the girth portion.

A more detailed structure where a stretchable laminate sheet is used in a disposable diaper is disclosed in US2013/0110073A1 (WO2012/017817A1), for example, the disclosure of which is herein incorporated by reference in its entirety.

Figure 1A:
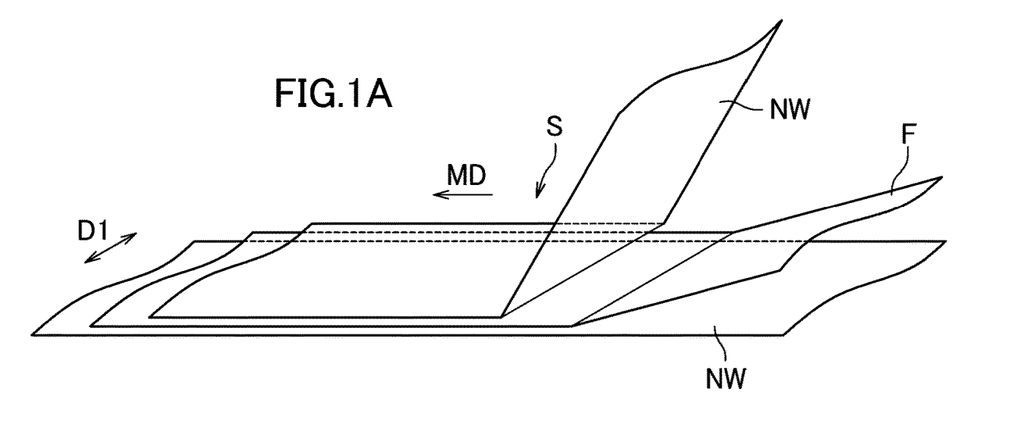
FIG. 1A is a schematic perspective view showing a macroscopic structure of a stretchable laminate sheet.

As shown in FIG. 1A, the present embodiment is directed to a case in which a thermoplastic stretchable film F is sandwiched between a pair of non-woven fabrics NW containing thermoplastic fiber therein. However, the stretchable film F may be laminated on a single sheet of non-woven fabric NW, thereby forming a stretchable laminate sheet S.

Figure 2A:
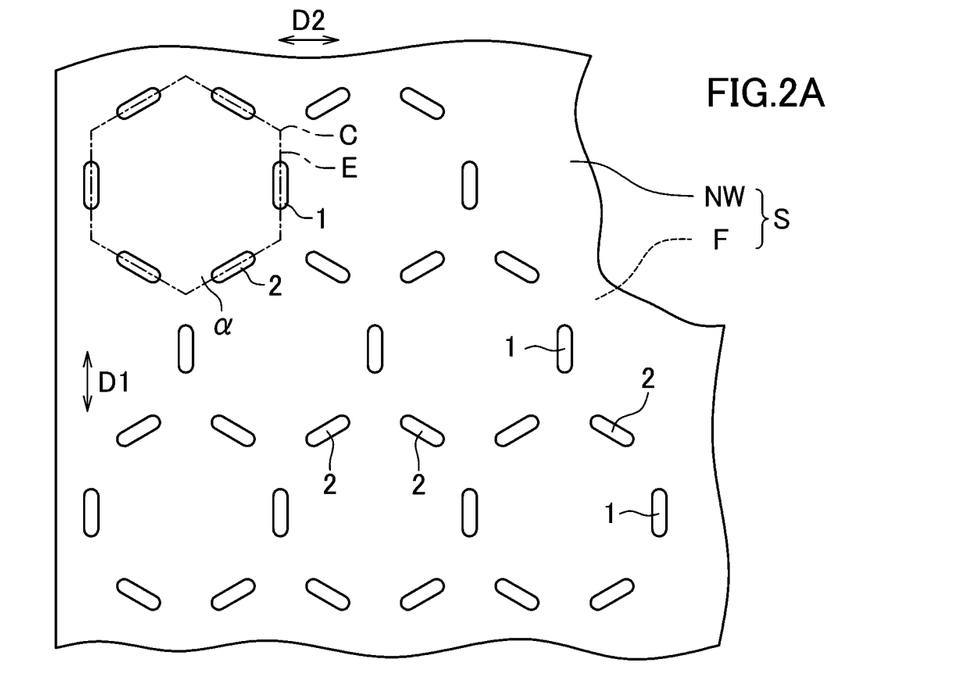
FIG. 2A is a schematic plan view microscopically showing the shape, the size, etc., of welding portions according to an embodiment of the present invention.

The pair of non-woven fabrics NW and the stretchable film F are welded and laminated together at a large number of oblong circular first and second welding portions 1 and 2 shown in FIG. 2A. The stretchable laminate sheet S may be used in the flap or the girth portion of a disposable diaper, for example. In this case, the girth direction D2 is the stretch direction D2 in which the stretchable laminate sheet S stretches. In the present embodiment, the stretch direction D2 is the second direction D2.

The welding portions 1 and 2 may be formed by the vibration energy of an ultrasonic horn or may be formed by heating to raise the temperature.

In the present embodiment, the first welding portion 1 has an oblong circular shape that is longer in the first direction D1 and shorter in the second direction D2 perpendicular to the first direction D1. That is, as shown in FIG. 3, the first length L1 of the first welding portion 1 in the first direction D1 is greater than the first width W1 of the first welding portion 1 in the stretch direction D2.

Figure 3:
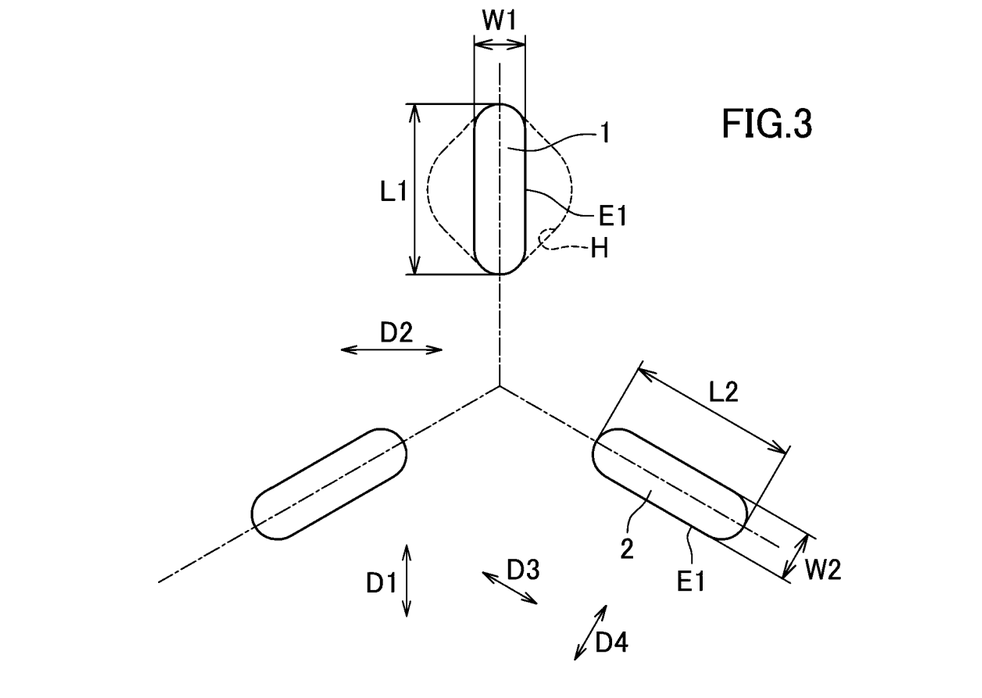
FIG. 3 is an enlarged view of first and second welding portions of a stretchable laminate sheet.

As shown in FIG. 3, the second welding portion 2 has an oblong circular shape that is longer in the third direction D3 crossing the first direction D1 and shorter in the fourth direction D4 perpendicular to the third direction D3. That is, the second length L2 of the second welding portion 2 in the third direction D3 is greater than the second width W2 of the second welding portion 2 in the fourth direction D4.

In FIG. 2A, the one-dot-chain line represents a virtual polygonal shape having four or more sides, e.g., a hexagonal shape. The first and second welding portions 1 and 2 are absent (not arranged) at corners C of the virtual hexagonal shape, and are arranged along the sides E of the polygonal shape. The area a, represented by the one-dot-chain line, surrounded by the corners C of the hexagonal shape and the first and second welding portions 1 and 2 is a non-welding portion where the non-woven fabric NW and the stretchable film F are not welded together.

Now, if the stretchable laminate sheet S is pulled in the girth direction, i.e., in the second direction D2, when the worn article is put on, the stretchable laminate sheet S stretches in the second direction D2. Then, as shown in FIG. 3, in the area along the long side E1 of the first welding portion 1 perpendicular to the second direction, the stretchable film F between the pair of non-woven fabrics NW is likely to stretch in the second direction D2 and is likely to break. Thus, a large hole H as indicated by a broken line is likely to be formed in the stretchable film F. That is, by the pulling, holes are not formed in the pair of non-woven fabrics NW having a higher strength, but holes are formed only in the stretchable film F sandwiched between the pair of non-woven fabrics NW. Note that FIG. 3 is an enlarged plan view of the stretchable laminate sheet S including the stretchable film F sandwiched between the pair of non-woven fabrics NW.

On the other hand, the second welding portion 2 shown in FIG. 3 is inclined with respect to the second direction D2 relative to the first welding portion 1. Therefore, when a tension acts in the second direction D2, the stretchable film F will not stretch so much in the area along the long side E1 of the second welding portion 2. Therefore, holes H (not shown) formed in the stretchable film F around the second welding portions 2 will be smaller than those around the first welding portion 1 or there may be no holes H.

Figure 1B:
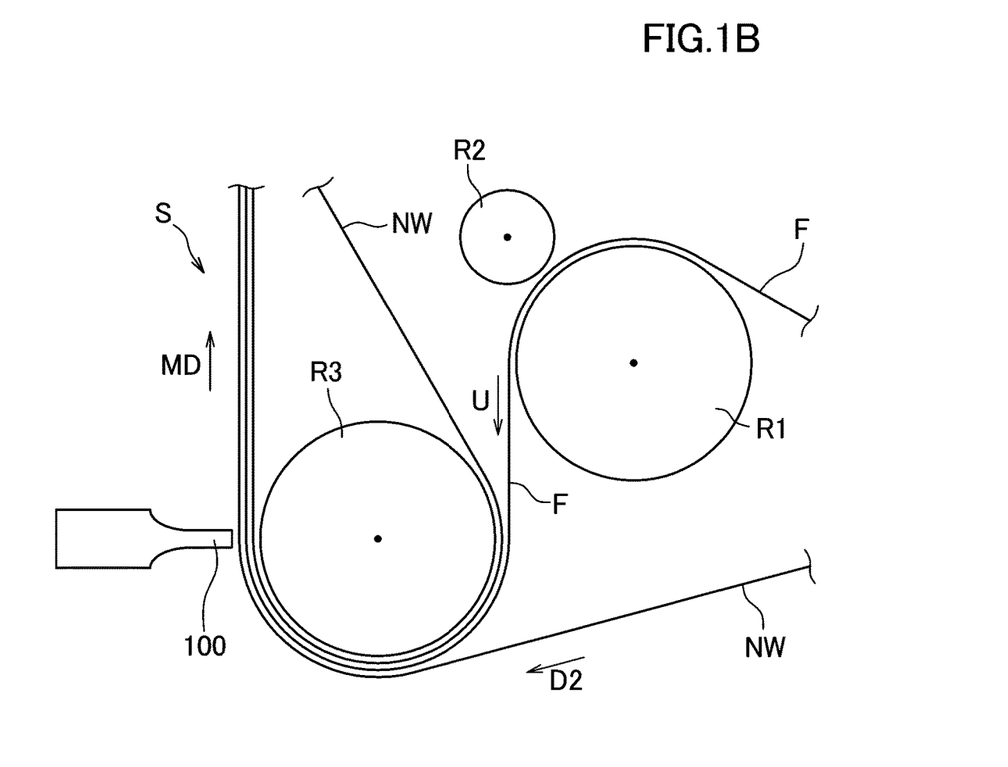
FIG. 1B is a schematic front view showing a device for manufacturing a stretchable laminate sheet.

FIG. 1B shows a device for manufacturing the stretchable laminate sheet S.

In FIG. 1B, the film F is sandwiched between a pair of nip rolls R1 and R2, and is supplied toward an anvil roll R3 from between the nip rolls. On the other hand, the pair of non-woven fabrics NW are wound around the anvil roll R3 in such a manner that the stretchable film F is sandwiched therebetween. An ultrasonic horn 100 gives a vibration energy to the three-layer sheet-like material. The layers of the sheet-like material are welded (sealed) together at protrusions formed on the surface of the anvil roll R3 that have the shape and the arrangement in conformity with the welding pattern of FIG. 2A.

The stretchable film F is laminated with the non-woven fabric with a tension applied thereto. When a tension is applied to the stretchable film F of FIG. 1A, it shrinks (neck-in) in the width direction D1. Therefore, it is preferred to apply a tension to the stretchable film F immediately before welding the stretchable film. Therefore, it is preferred that the pair of nip rolls R1 and R2 are arranged upstream of and in the vicinity of the ultrasonic horn 100 and the anvil roll R3, as shown in FIG. 1B.

In the present manufacturing device, the stretchable film F having been fed out of the pair of nip rolls R1 and R2 is sandwiched between the pair of non-woven fabrics at the anvil roll R3 below the nip rolls. Therefore, even when the stretchable film F under a tension is severed between the nip rolls R1 and R2 and the anvil roll R3, the tip of the severed stretchable film F is sandwiched between the pair of non-woven fabrics below. Therefore, it is possible to continuously manufacture the stretchable laminate sheet without stopping the manufacturing device.

In the manufacturing process, the non-woven fabrics NW and the stretchable film F of FIG. 1A are continuous in the carrying direction MD.

Figure 2B:
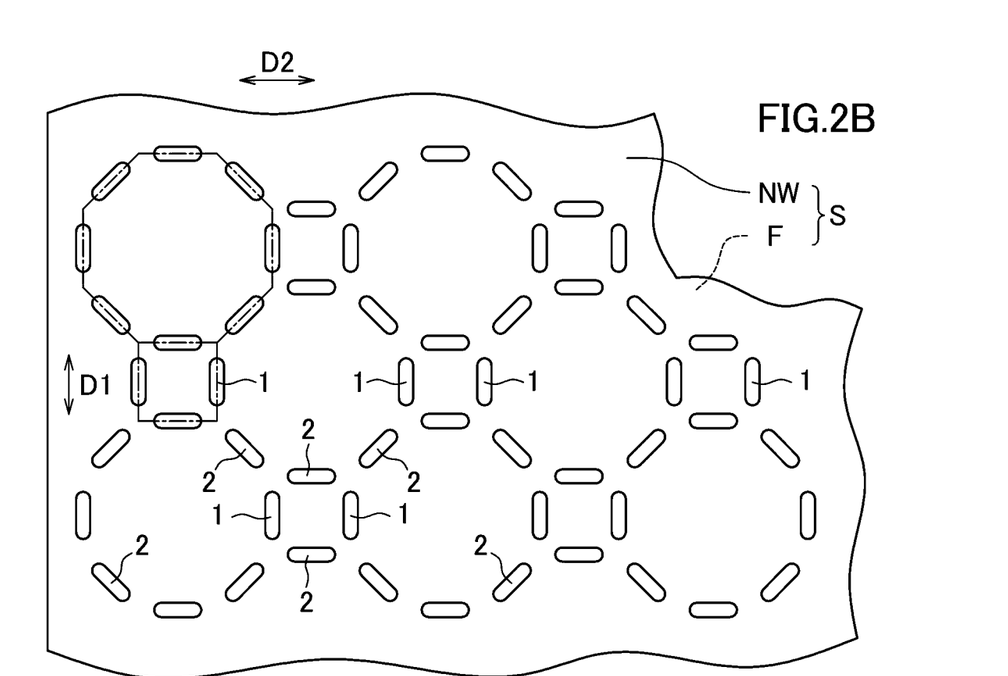
FIG. 2B is a schematic plan view showing another example.

FIG. 2B shows another welding pattern.

As shown in the figure, the polygonal shape may be a pattern including rectangular shapes and octagonal shapes vertically and horizontally alternating with each other.

A structure of a sheet according to Embodiment 2 of the present invention will now be described with reference to the drawings.

Figure 4A:
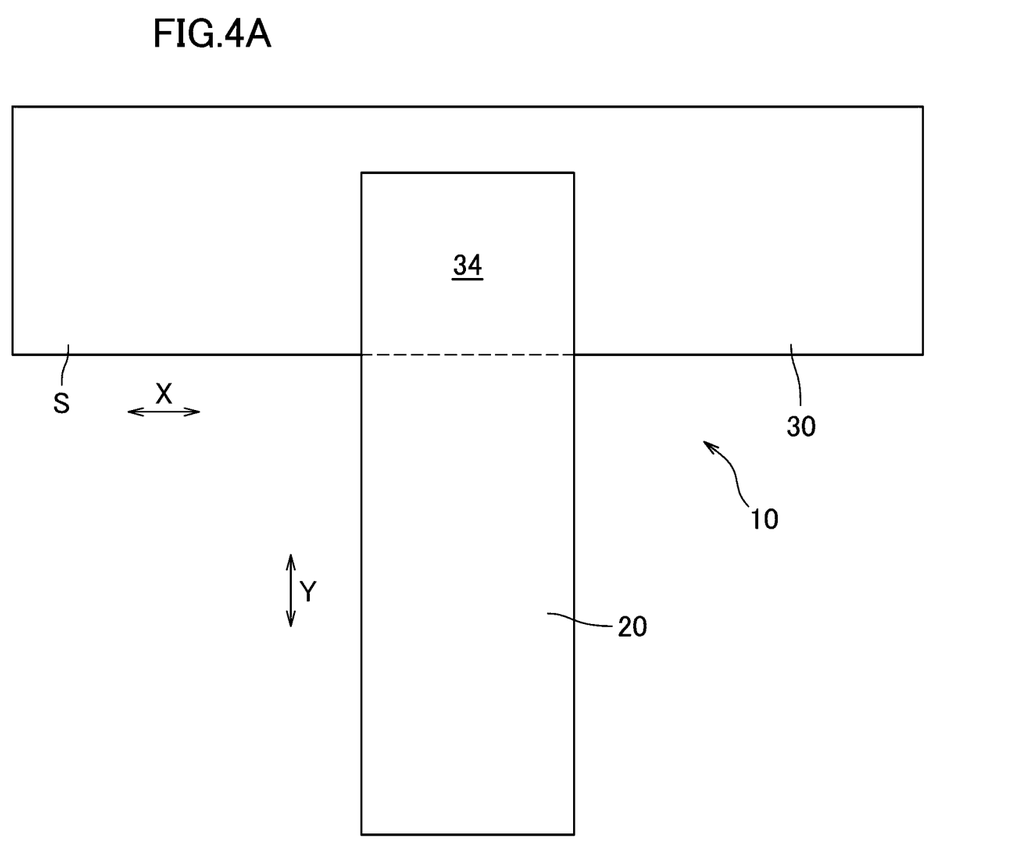
FIG. 4A and FIG. 4B are each a schematic plan view showing a worn article whose gathers are stretched vertically and horizontally.
Figure 4B:
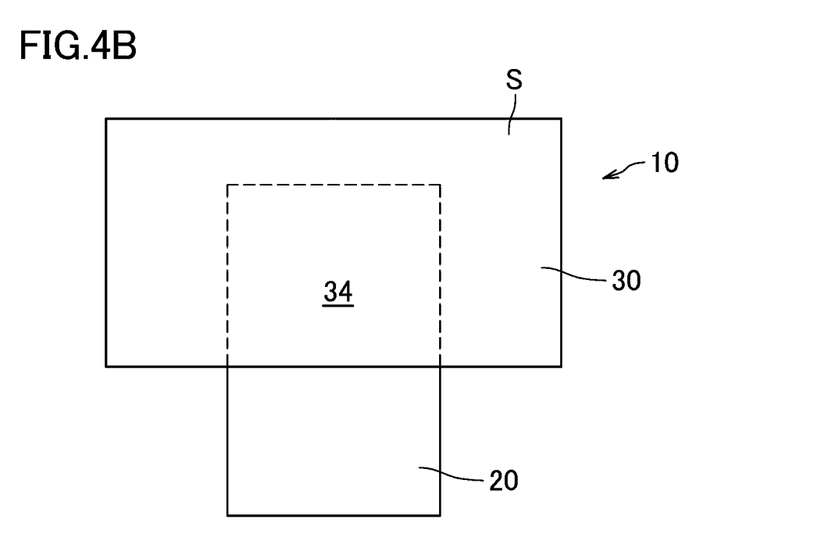

FIG. 4A and FIG. 4B show a worn article.

As shown in these figures, a worn article 10 includes an absorbent body 20 and a girth portion 30. The absorbent body 20 extends in the vertical direction Y perpendicular to the girth direction X. The worn article 10 may be a diaper-type worn article of FIG. 4A or may be a pants-type worn article of FIG. 4B.

An absorbent core (not shown) is provided on the absorbent body 20. The absorbent core absorbs body fluid. The absorbent core is sandwiched between the top sheet and the back sheet. The sheets and the absorbent core are layered together.

The top sheet is formed from a liquid-permeable thin non-woven fabric and covers the skin-contact surface of the absorbent core. A cuff (not shown) may be provided on the top sheet.

The back sheet covers the non-skin-contact surface of the absorbent core and is formed from a liquid-impermeable resin sheet. The girth portion 30 is attached to an end portion in the vertical direction Y of the absorbent body 20. That is, the girth portion 30 includes an overlap portion 34 where the absorbent body 20 is laid on the girth portion 30.

The girth portion 30 is formed from the stretchable laminate sheet S, and is configured so as to extend in the girth direction X of the wearer and cover the torso of the wearer. The absorbent body 20 is configured to cover the crotch of the wearer.

Figure 5A:
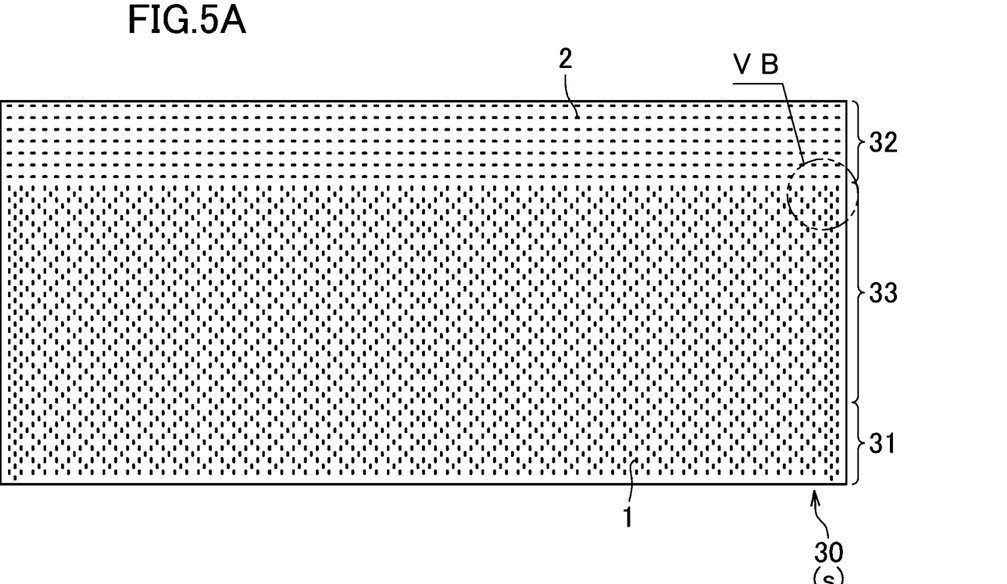
FIG. 5A is a schematic plan view showing a girth portion, which is an example of a stretchable laminate sheet, being stretched in the girth direction and in the vertical direction.
Figure 5B:
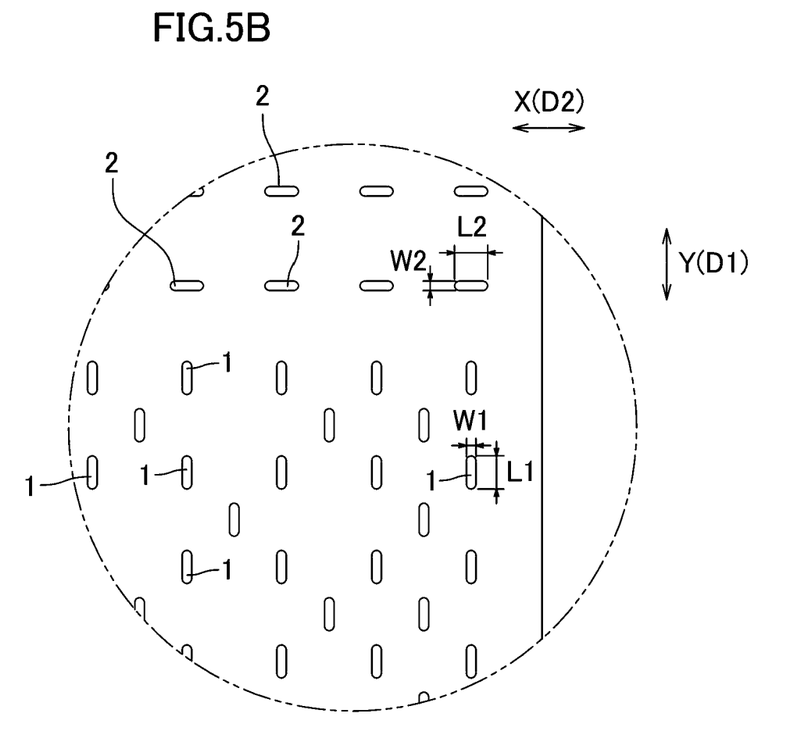
FIG. 5B is an enlarged plan view showing the area VB of FIG. 5A on an enlarged scale.

FIG. 5A and FIG. 5B show an example of the stretchable laminate sheet S forming the girth portion 30.

The second welding portions 2 are provided in rows and columns (in a matrix pattern) in an upper edge portion 32 of the girth portion 30. The first welding portions 1 are provided in rows and columns (in a matrix pattern) in a lower edge portion 31 and a middle portion 33 of the girth portion 30. The first welding portions 1 and the second welding portions 2 are arranged intermittently in the girth direction X (the first direction D1) and arranged intermittently in the vertical direction Y (the second direction D2).

The middle portion 33 is a portion between the lower edge portion 31 and the upper edge portion 32, excluding the lower edge portion 31 and the upper edge portion 32. Typically, the upper edge portion 32 is referred to as the waist portion, and the lower edge portion 31 and the middle portion 33 as the hip portion.

The first length L1 of the first welding portions 1 defined in the vertical direction Y perpendicular to the girth direction X is greater than the first width thereof defined in the girth direction X. The second welding portions 2 are larger in the girth direction X than the second width W2 thereof in the vertical direction.

In the case of this example, holes H as indicated by a broken line of FIG. 3 are formed in the first welding portion 1 when worn.

Figure 6A:
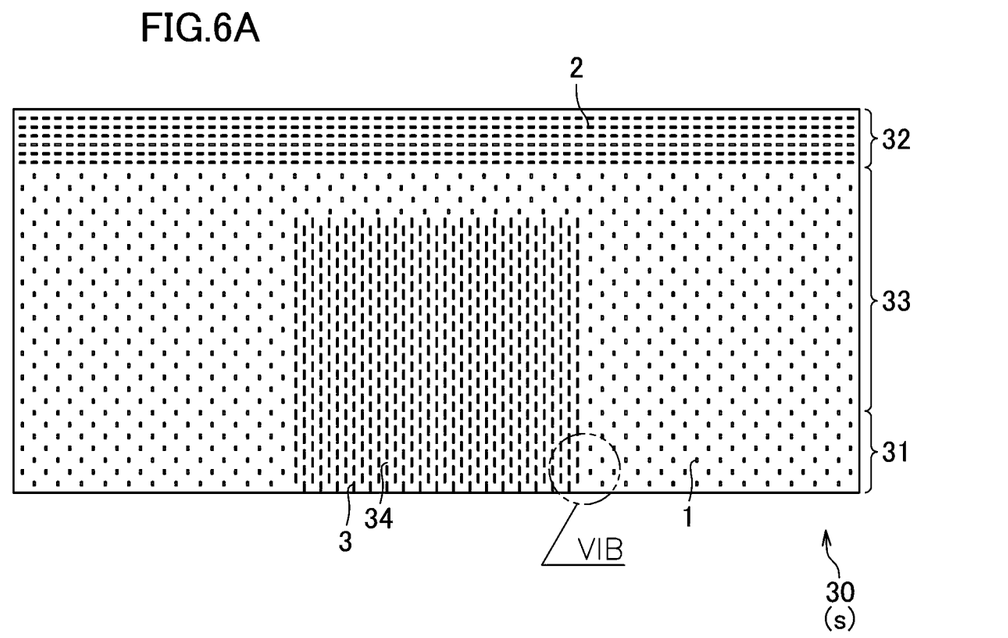
FIG. 6A is a schematic plan view showing another girth portion.
Figure 6B:
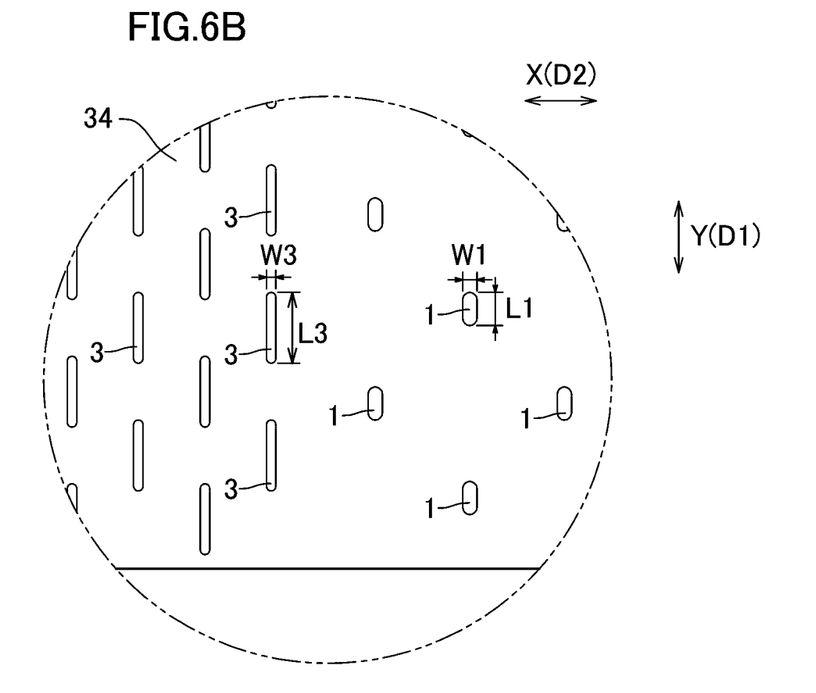
FIG. 6B is an enlarged plan view showing the area VIB of FIG. 6A on an enlarged scale.

FIG. 6A and FIG. 6B show another example of the stretchable laminate sheet S.

In the case of this example, the non-woven fabrics NW and the stretchable film F of FIG. 1A are welded together at a plurality of third welding portion 3 of FIG. 6A in the overlap portion 34 of FIG. 6A. The overlap portion 34 is provided in the central area in the girth direction X of the lower edge portion 31 and the middle portion 33.

The third welding portions 3 of FIG. 6B have a longer third length L3 in the vertical direction Y, which is the first direction D1, and have a third width W3, shorter than the third length, in the girth direction X, which is the second direction D2. The third length L3 of the third welding portions 3 is greater than the first length L1 of the first welding portions 1.

The third welding portions 3 are provided in rows and columns (in a matrix pattern) in the overlap portion 34. The third welding portions 3 are arranged intermittently in the girth direction X (the first direction D2) and arranged intermittently in the vertical direction Y (the second direction D1).

The ratio of the third length L3 with respect to the third width W3 of the third welding portions 3 of FIG. 6B is greater than the ratio of the first length L1 with respect to the first width W1 of the first welding portions 1.

Otherwise, the configuration of the example of FIG. 6A and FIG. 6B is similar to that of the example of FIG. 5A and FIG. 5B, and will not be further described below.

Figure 7A:
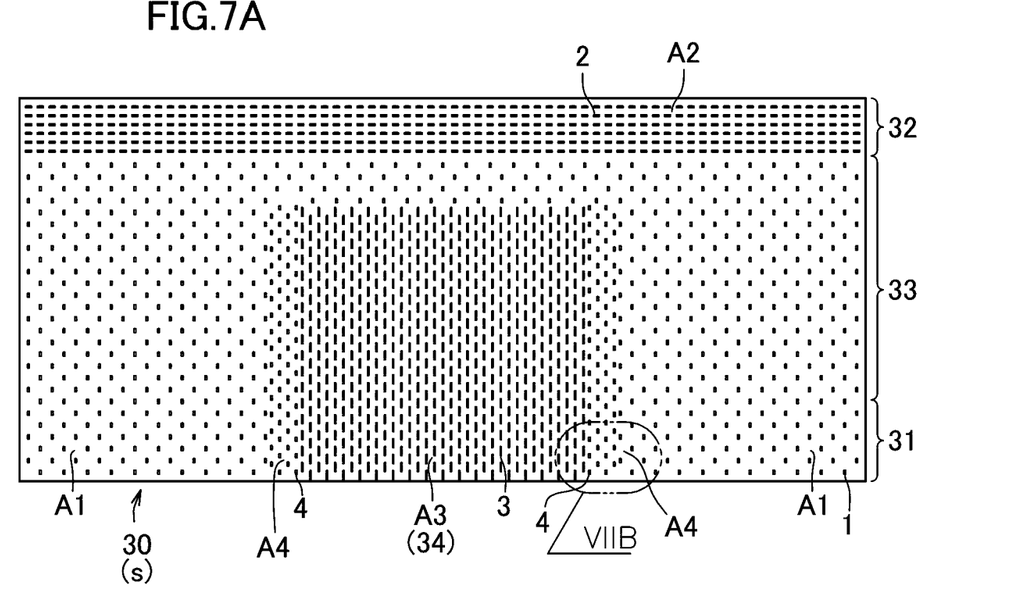
FIG. 7A is a schematic plan view showing another girth portion.
Figure 7B:
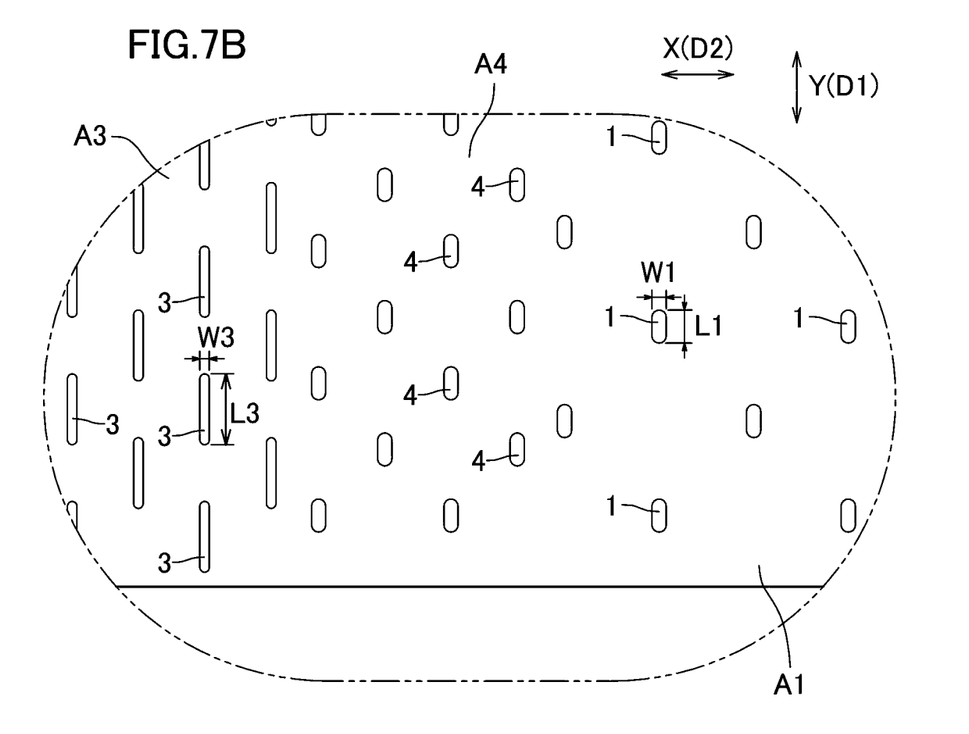
FIG. 7B is an enlarged plan view showing the area VIIB of FIG. 7A on an enlarged scale.

FIG. 7A and FIG. 7B show still another example of the stretchable laminate sheet S.

In the case of this example, the configuration is such that the area ratios of the various welding portions change gradually along the girth direction X as will be described below.

A fourth region A4 is arranged between a first region A1 where the first welding portions 1 are provided and a third region A3 where the third welding portions 3 are provided. In the fourth region A4, the non-woven fabrics NW and the stretchable film F (FIG. 1A) are welded together at a plurality of fourth welding portions 4. Note that the upper edge portion 32 where the second welding portions 2 are provided belongs to a second region A2.

The ratio C4 of the total area of the fourth welding portions 4 with respect to the area of the fourth region A4 is greater than the ratio C1 of the total area of the first welding portions 1 with respect to the area of the first region A1. The ratio C4 is less than a ratio C3 of the total area of the third welding portions 3 with respect to the area of the third region A3. That is, in the lower edge portion 31 and the middle portion 33, the ratio of the area of welding portions in a region with respect to the area of the region gradually increases toward the overlap portion 34.

Otherwise, the configuration of the example of FIG. 7A and FIG. 7B is similar to that of the example of FIG. 6A and FIG. 6B, and will not be further described below. Note that the description of the example below will focus on differences from the examples of FIG. 5A to FIG. 7B.

Figure 8A:
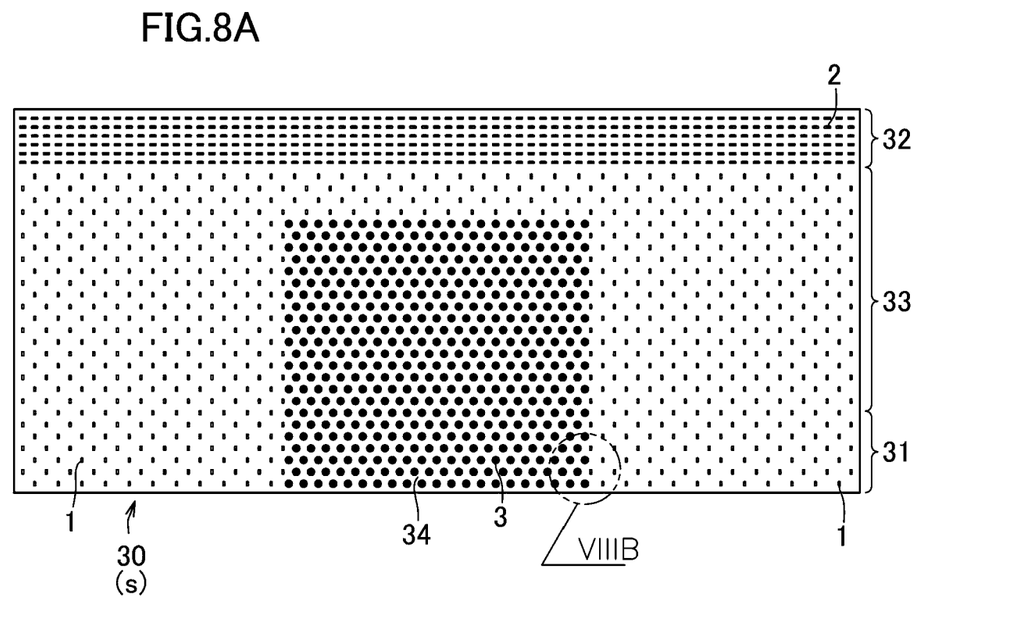
FIG. 8A is a schematic plan view showing another girth portion.
Figure 8B:
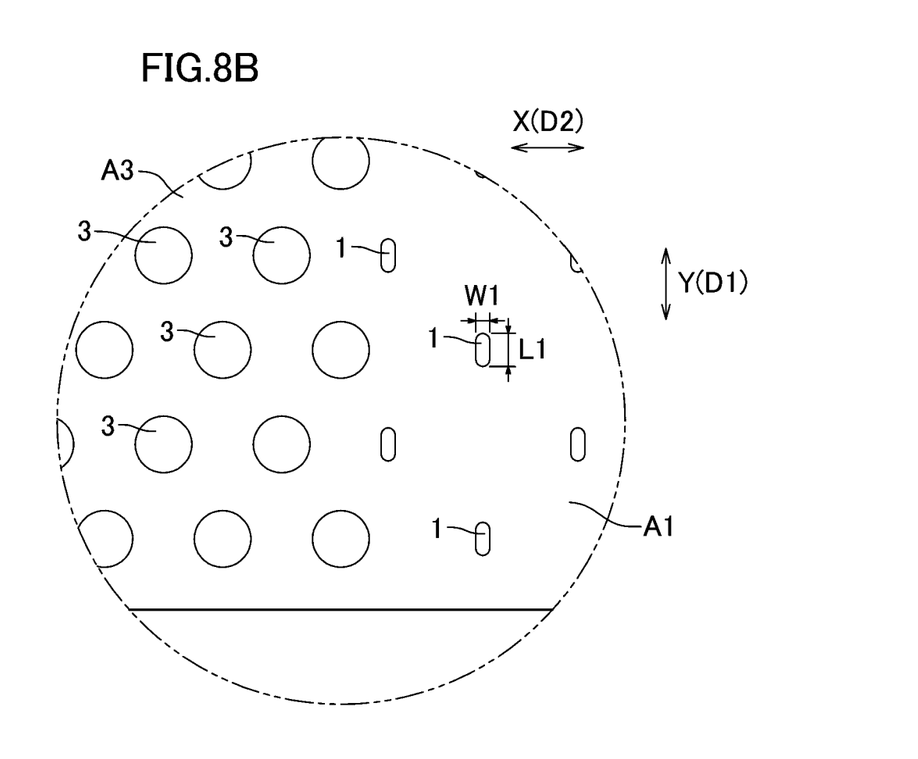
FIG. 8B is an enlarged plan view showing the area VIII of FIG. 8A on an enlarged scale.

As shown in the example of FIG. 8A and FIG. 8B, the third welding portions 3 may have a circular shape. The fourth welding portions 4 may be absent.

In this case, however, the ratio C3 of the third region A3 is significantly greater than the ratio C1 of the first region A1. Therefore, the horn contact pressure per unit area fluctuates rapidly during the welding process by means of the horn 100 (FIG. 1). This may cause a decrease in the reliability of the ultrasonic welding.

Figure 9A:
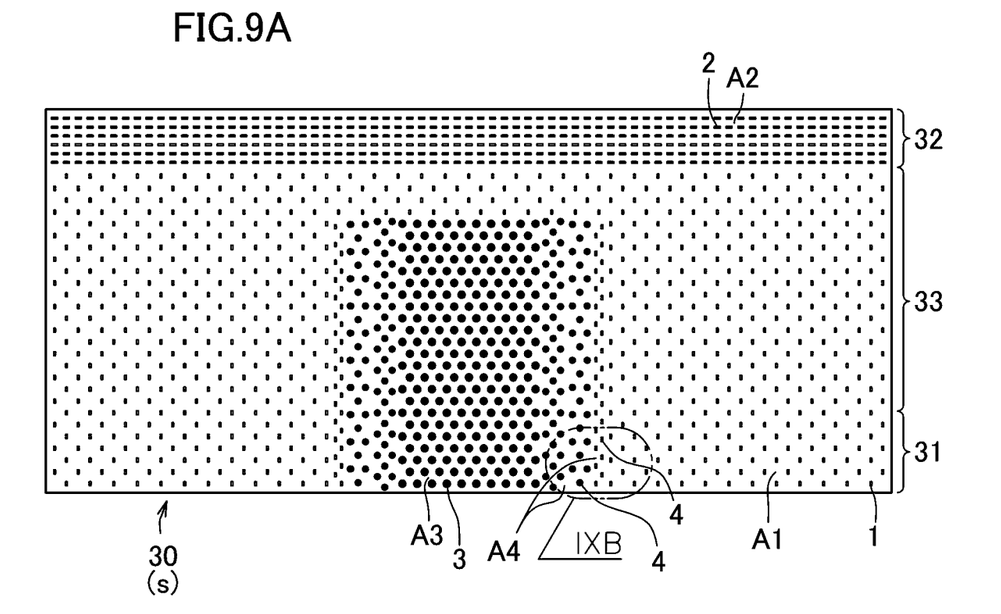
FIG. 9A is a schematic plan view showing another girth portion.
Figure 9B:
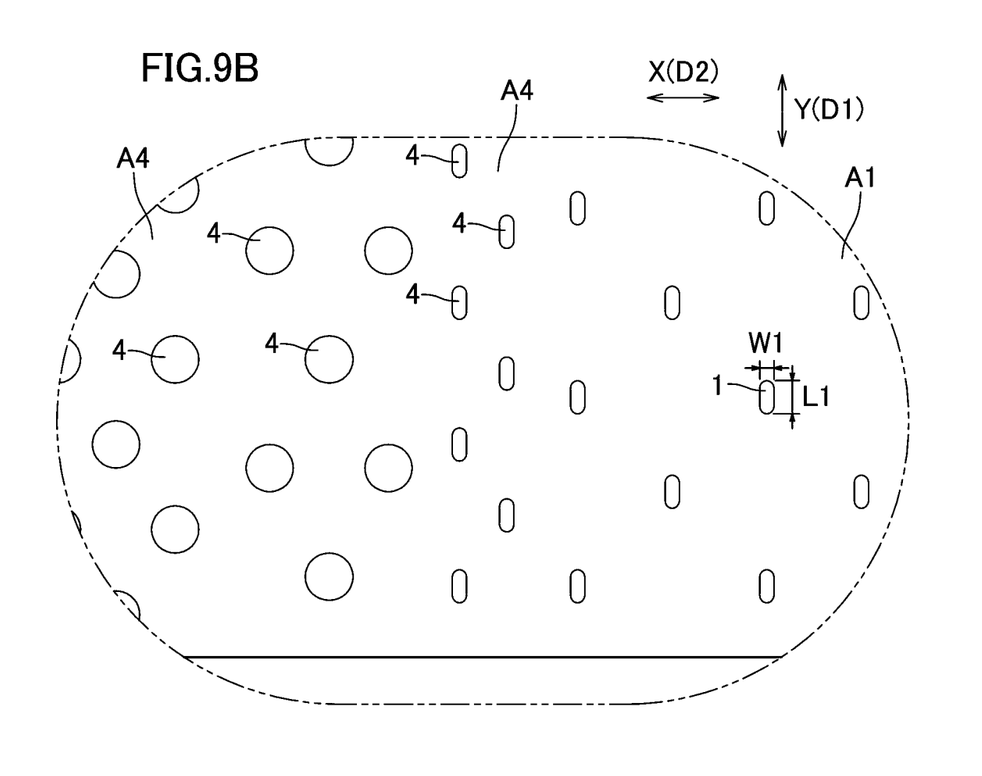
FIG. 9B is an enlarged plan view showing the area IXB of FIG. 9A on an enlarged scale.

In contrast, as shown in the example of FIG. 9A and FIG. 9B, even when the third welding portions 3 have a circular shape, if the fourth welding portions 4 are provided, the ratios C3, C4 and C1 of the various regions change gradually. Therefore, it is possible to suppress the rapid fluctuation of the horn contact pressure.

Note that as can be seen from FIG. 9A, two types of fourth welding portions 4 may be provided so that the change in the area ratio will be more gradual.

The ratios C3, C4 and C1 for the different regions may be set as follows.

The ratios C1, C3 and C4 for the different regions of FIG. 7A may be defined by the following expressions, for example.

$$1.0\% < C1 < 4.0\% \tag{71}$$

$$4.0\% < C4 < 6.0\% \tag{74}$$

$$6.0\% < C3 < 10\% \tag{73}$$

The ratios C1, C3 and C4 for the different regions of FIG. 9A may be defined by the following expressions, for example.

$$1.0\% < C1 < 5.0\% \tag{91}$$

$$5.0\% < C4 < 20\% \tag{94}$$

$$20\% < C3 < 30\% \tag{93}$$

Figure 10A:
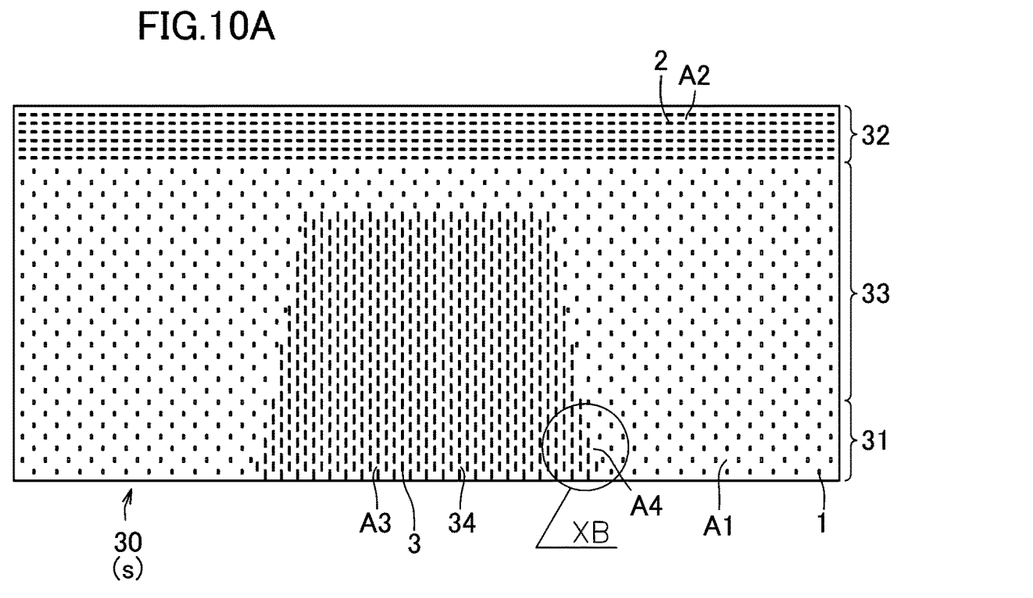
FIG. 10A is a schematic plan view showing another girth portion.
Figure 10B:
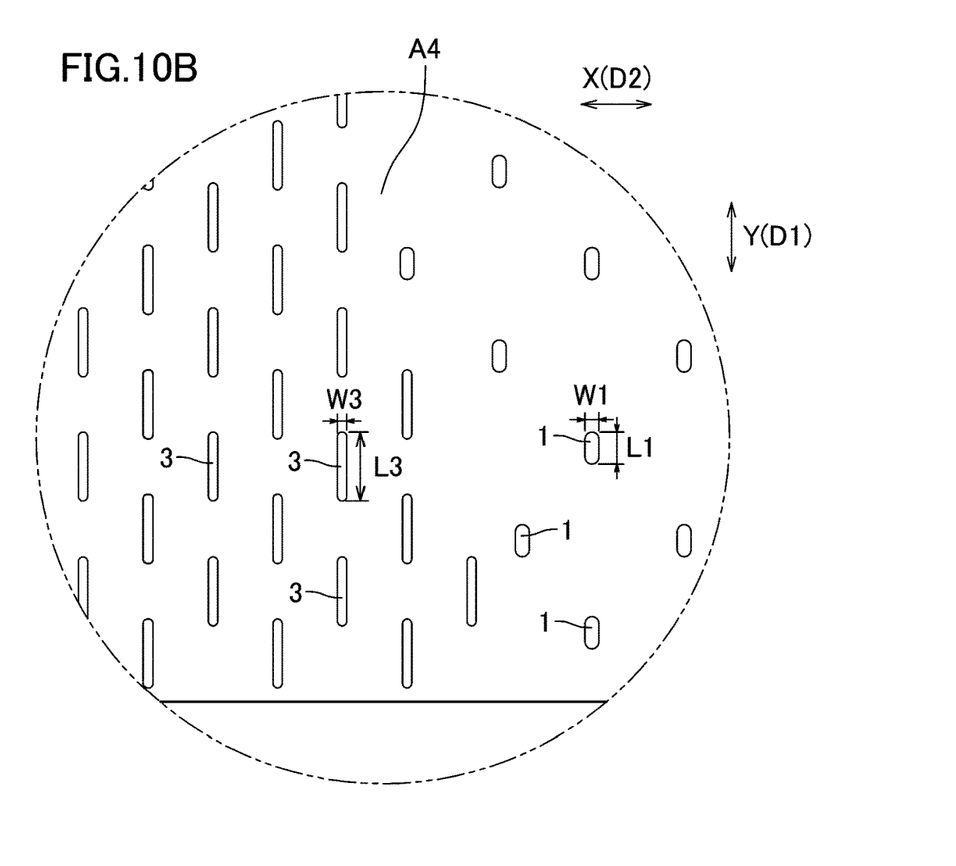
FIG. 10B is an enlarged plan view showing the area X of FIG. 10A on an enlarged scale.

As shown in the example of FIG. 10A and FIG. 10B, the boundary between the first region A1 and the third region A3 may be set to be diagonal. In such a case, the change in the area ratio in the boundary area will be even more gradual, i.e., nearly continuous.

While preferred embodiments have been described above with reference to the drawings, obvious variations and modifications will readily occur to those skilled in the art upon reading the present specification.

For example, one or both of the non-woven fabrics NW may be a non-continuous non-woven fabric rather than a continuous non-woven fabric. A single sheet of stretchable film F may be laminated with a single sheet of non-woven fabric NW. The non-woven fabric may be non-stretchable.

The shape of the first welding portions and the shape of the second welding portions may be different from each other. The first length of the first welding portions and the second length of the second welding portions may be equal to each other or different from each other. The first width of the first welding portions and the second width of the second welding portions may be equal to each other or different from each other. The shape of the welding portions may be an elliptical shape rather than an oblong circular shape. The polygonal shape may be a regular polygonal shape as illustrated in the embodiments, or may not be a regular polygonal shape.

Thus, such changes and modifications are deemed to fall within the scope of the present invention, which is defined by the appended claims.

INDUSTRIAL APPLICABILITY

The stretchable laminate sheet of the present invention is applicable to a part of a member of a disposable worn article, or the like.

REFERENCE SIGNS LIST

1: First welding portion, 2: Second welding portion, 3: Third welding portion, 4: Fourth welding portion
A1 to A4: First to fourth regions
NW: Non-woven fabric, F: Stretchable film, S: Stretchable laminate sheet
D1: First direction, D2: Second direction, D3: Third direction, D4: Fourth direction, MD: Carrying direction
E1: Long side, H: Hole
L1: First length, L2: Second length, L3: Third length, W1: First width, W2: Second width
W3: Third width
R1, R2: Nip roll, R3: Anvil roll
X: Girth direction, Y: Vertical direction
20: Absorbent body, 30: Girth portion
31: Lower edge portion, 32: Upper edge portion, 33: Middle portion, 34: Overlap portion

The invention claimed is:

1. A disposable worn article including a stretchable laminate sheet, the disposable worn article including:
a girth portion formed from the stretchable laminate sheet, extending in a girth direction of a wearer, and configured to cover a torso of the wearer, the girth portion including a lower edge portion, an upper edge portion, and a middle portion between the lower edge portion and the upper edge portion; and
an absorbent body configured to cover a crotch of the wearer;
wherein:
the stretchable laminate sheet includes a thermoplastic stretchable film laminated on a non-woven fabric containing thermoplastic fiber therein;
the non-woven fabric and the stretchable film are welded together at a plurality of first welding portions and a plurality of second welding portions;
the first welding portions each have a longer first length in a first direction, and each have a first width, shorter than the first length, in a second direction perpendicular to the first direction;
the second welding portions each have a longer second length in a third direction crossing the first direction, and each have a second width, shorter than the second length, in a fourth direction perpendicular to the third direction;
the first welding portions are provided in the lower edge portion and the middle portion of the girth portion;
the second welding portions are provided in the upper edge portion of the girth portion;
the first welding portions are arranged intermittently in the girth direction and arranged intermittently in a vertical direction perpendicular to the girth direction;
the second welding portions are arranged intermittently in the girth direction and arranged intermittently in the vertical direction;
a length of each of the first welding portions in the vertical direction perpendicular to the girth direction is longer than a length thereof in the girth direction; and
a length of each of the second welding portions in the girth direction is longer than a length thereof in the vertical direction.

2. The disposable worn article according to claim 1, wherein:
the girth portion includes an overlap portion where the absorbent body is laid on the girth portion;

the non-woven fabric and the stretchable film are welded together at a plurality of third welding portions in the overlap portion;

the third welding portions each have a longer third length in the vertical direction, which is the first direction, and have a third width, shorter than the third length, in the girth direction, which is the second direction; and the third length of the third welding portions is longer than the first length of the first welding portions.

3. The disposable worn article according to claim 2, wherein the third width of the third welding portions is smaller than the first width of the first welding portions.

4. The disposable worn article according to claim 2, wherein a ratio of the third length of the third welding portions with respect to the third width thereof is greater than a ratio of the first length of the first welding portions with respect to the first width thereof.

5. The disposable worn article according to claim 1, wherein:

the girth portion includes an overlap portion where the absorbent body is laid on the girth portion;

the non-woven fabric and the stretchable film are welded together at a plurality of third welding portions in the overlap portion;

a fourth region is arranged between a first region where the first welding portions are provided and a third region where the third welding portions are provided, and the non-woven fabric and the stretchable film are welded together at a plurality of fourth welding portions in the fourth region; and a ratio of a total area of the fourth welding portions with respect to an area of the fourth region is greater than a ratio of a total area of the first welding portions with respect to an area of the first region and is less than a ratio of a total area of the third welding portions with respect to an area of the third region.

* * * * *